(12) United States Patent
Becker et al.

(10) Patent No.: US 8,361,529 B2
(45) Date of Patent: Jan. 29, 2013

(54) XYLANASE

(75) Inventors: Fiona Becker, Virum (DK); Tine Hoff, Holte (DK); Henrik Lundquist, Malmo (SE); Tina Spendler, Malov (DK)

(73) Assignee: Novozymes A/S, Bagsvaerd (DK)

( * ) Notice: Subject to any disclaimer, the term of this patent is extended or adjusted under 35 U.S.C. 154(b) by 694 days.

(21) Appl. No.: 10/588,298

(22) PCT Filed: Jan. 20, 2005

(86) PCT No.: PCT/DK2005/000034
§ 371 (c)(1),
(2), (4) Date: Apr. 20, 2007

(87) PCT Pub. No.: WO2005/079585
PCT Pub. Date: Sep. 1, 2005

(65) Prior Publication Data
US 2007/0224325 A1    Sep. 27, 2007

Related U.S. Application Data

(60) Provisional application No. 60/547,301, filed on Feb. 23, 2004.

(30) Foreign Application Priority Data

Feb. 20, 2004  (DK) ................................ 2004 00263

(51) Int. Cl.
*A21D 2/08* (2006.01)
(52) U.S. Cl. ........ 426/555; 426/594; 426/653; 435/243; 435/320.1; 435/71.1; 530/350
(58) Field of Classification Search .................. 426/555, 426/594, 653; 435/243, 320.1, 71.1; 530/350
See application file for complete search history.

(56) References Cited

U.S. PATENT DOCUMENTS

| 6,254,903 | B1 * | 7/2001 | Schuster et al. ................. 426/52 |
| 2003/0059902 | A1 * | 3/2003 | Cherry et al. .................. 435/101 |
| 2004/0028773 | A1 | 2/2004 | Sturkenboon et al. |

FOREIGN PATENT DOCUMENTS

| WO | WO 95/23515 | | 9/1995 |
| WO | WO 96/32472 | | 10/1996 |
| WO | WO 00/39289 | | 7/2000 |
| WO | WO 03/020923 | * | 3/2003 |
| WO | WO 03/106654 | | 12/2003 |

OTHER PUBLICATIONS

Watanabe, S. et al. 2003. Cloning, Expression, and cell surface localization of *Peanibacillus* sp. strain W-61 xylanase 5, a multidomain xylanase. Appl. Environ. Microbiol. 69(12) 6969-6978.*
Viet, D. N. et al. 1991. Purification and properties of beta-1,4-xylanase from Aeromonas caviae W-61. Appl. Environ. Microbiol. 57:445-449.*
Nucleotide-Amino-Acid Search Report-Database Uniprot. ID-Q1XGE6-9BACL.*
EMBL-EBI, Accession # D32065, (1994).
EMBL-EBI, Accession # AF195421, (2000).
Kubata et al, Bio Science Biotech, Biochemistry, vol. 56, Part 9, pp. 1463-1464 (1992).

* cited by examiner

*Primary Examiner* — D. Lawrence Tarazano
*Assistant Examiner* — Hamid R Badr
(74) *Attorney, Agent, or Firm* — Kristin J. McNamara

(57) ABSTRACT

The inventors have identified a xylanase from a bacterial strain of *Paenibacillus pabuli* and found that the xylanase can increase the shelf life of baked products. More specifically, the xylanase in combination with a maltogenic amylase further improves the softness of bread crumb without having detrimental effects on elasticity.

8 Claims, No Drawings

XYLANASE

CROSS-REFERENCE TO RELATED APPLICATIONS

This application is a 35 U.S.C. 371 national application of PCT/DK2005/000034 filed Jan. 20, 2005, which claims priority or the benefit under 35 U.S.C. 119 of Danish application no. PA 2004 00263 filed Feb. 20, 2004 and U.S. provisional application No. 60/547,301 filed Feb. 23, 2004, the contents of which are fully incorporated herein by reference.

FIELD OF THE INVENTION

The present invention relates to a process for preparing a dough-based product and to a xylanase for use in the process.

BACKGROUND OF THE INVENTION

K. B. Kubata et al., *Biosci. Biotech. Biochem.*, 56 (9), 1463-1464 (1992) describes Xylanase I of *Aeromonas caviae* ME-1. Its amino acid sequence was submitted by T. Suzuki et al. in 1994 to the EMBL/GenBank/DDBJ databases where it was given the accession number Q43993.

WO 0039289 describes a xylanase from *Bacillus subtilis* said to be suitable for preparing non-sticky dough.

SUMMARY OF THE INVENTION

The inventors have identified a xylanase from a bacterial strain of *Paenibacillus pabuli* and found that the xylanase can increase the shelf life of baked products. More specifically, the xylanase in combination with a maltogenic amylase further improves the softness of bread crumb without having detrimental effects on elasticity.

Accordingly, the invention provides a process for preparing a dough-based product, comprising adding a xylanase with a high identity to SEQ ID NO: 2 to a dough, leavening, and heating the dough. More specifically, the xylanase is a polypeptide having at least 83% identity to the amino acid sequence as shown in positions 1-182 of SEQ ID NO 2 or encoded by a nucleic acid sequence which hybridizes at 38° C. in 0.1×SSC with the complementary strand of nucleotides 85-630 of SEQ ID NO: 1.

The invention further provides a dough composition which comprises flour together with the xylanase and a dough and/or bread-improving additive comprising the xylanase in the form of a granulate or agglomerated powder.

The invention also provides a polypeptide having xylanase activity. It may be a polypeptide encoded by the genome present in *Paenibacillus* DSM 16232 that can be amplified with the primers (SEQ ID NO.: 3) and (SEQ ID NO.: 4) or having an amino acid sequence as shown in positions 1-182 of SEQ ID NO 2, or it may be at least 95% identical to one of these. The polypeptide may also be encoded by a nucleic acid sequence which hybridizes at 49° C. in 0.1×SSC with the complementary strand of nucleotides 85-630 of SEQ ID NO: 1.

Alternatively, the xylanase may be a polypeptide having an amino acid sequence which can be obtained from the mature polypeptide of SEQ ID NO: 2 by substitution, deletion, and/or insertion of one or more amino acids and a polynucleotide having a sequence that can be derived from SEQ ID NO: 1 by substitution, deletion, and/or insertion of one or more nucleotides.

The invention also provides a polynucleotide encoding the xylanase, an expression vector comprising the polynucleotide, a transformed host cell comprising the vector, as well as a method of producing the xylanase by cultivating the transformant.

DETAILED DESCRIPTION OF THE INVENTION

Genomic DNA Source

The source organism of the xylanase of the invention is a bacterial strain isolated from soil samples collected in New Zealand in 1991. The strain was classified as belonging to *Paenibacillus pabuli*. The inventors have deposited the strain under the terms of the Budapest Treaty on 17 Feb. 2004 as DSM 16232 with the DSMZ—Deutsche Sammiung von Micro-organismen und Zelikulturen GmbH, Mascheroder-Weg 1b, D-38124 Braunschweig D E.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The polypeptide of the invention may be produced by transforming a suitable host cell with a DNA sequence encoding the xylanase enzyme, cultivating the transformed organism under conditions permitting the production of the enzyme, and recovering the enzyme from the culture.

The host organism may particularly be a prokaryotic cell, in particular a bacterial cell, such as gram positive bacteria including a *Bacillus* cell, e.g., *Bacillus lentus*, *Bacillus licheniformis*, *Bacillus stearothermophilus*, *Bacillus subtilis* or an alkalophilic *Bacillus*, or a *Streptomyces* cell, or gram negative bacteria such as *E. coli* and *Pseudomonas* sp.

Alignment and Identity

The polypeptide and polynucleotide of the invention may have identities to the disclosed sequences of at least 85%, at least 90%, at least 95% or at least 98%.

For purposes of the present invention, the alignments and identities of the protein sequences are analysed by Vector NTI—program (Invitrogen Corporation). The alignments are created using the Clustal W algorithm (Nucleic Acid Research, 22 (22): 4673-4680, 1994).

Alignment Parameters used for polypeptide alignments are: penalty for the first residue in a gap 10; penalty for additional residues in a gap 0.1; no penalty for gaps introduced at the end of a sequence.

Hybridization

Suitable conditions for determining hybridization between a nucleotide probe and a homologous DNA or RNA sequence involve presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6-13), $^{32}$P-dCTP-labeled (specific activity>$1\times10^9$ cpm/µg) probe for 12 hours at approx. 45° C. The filter is then washed two times for 30 minutes in 0.1×SSC, 0.5% SDS at a temperature of 25° C., 30° C., 35° C., 40° C., 45° C., 49° C. or 55° C. Molecules to which the oligonucleotide probe hybridizes under these conditions may be detected using a x-ray film.

Flour Composition or Dough

The flour composition may particularly comprise wheat flour. It may a dry mixture comprising flour and the xylanase, particularly in the form of the additive described above. The flour composition may also be a dough, which may be fresh, frozen or par-baked. It may be a laminated dough.

The xylanase may be added to the flour composition or dough at a dosage of 0.1-10 mg enzyme protein per kg of flour, particularly 0.2-5 mg/kg.

The dough may also comprise other conventional dough ingredients, e.g. proteins, such as milk powder and gluten; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate. The dough may comprise fat (triglyceride) such as granulated fat or shortening.

Additional Enzyme

Optionally, one or more additional enzymes may be added to the dough together with the xylanase of the invention. The additional enzyme may be an amylase, a lipolytic enzyme (e.g. as described in WO 9953769) or a second xylanase.

The amylase may be an exo-acting maltogenic alpha-amylase. An example is a maltogenic alpha-amylase from *B. stearothermophilus* strain NCIB 11837, available from Novozymes A/S under the tradename Novamyl®; described in WO 9104669 and having the amino acid sequence shown as SEQ ID NO: 1 of U.S. Pat. No. 6,162,628A1. Another example is a Novamyl variant, e.g. as described in WO 9943794. The maltogenic amylase may be added at a dosage of 100-1000 MANU per kg flour (MANU activity unit defined in WO 9104669).

Dough-Based Product

The invention provides a method for preparing a dough-based product by leavening the dough and heating it, e.g. by baking or steaming. The dough may be leavened e.g. by adding chemical leavening agents or yeast, usually *Saccharomyces cerevisiae* (baker's yeast). The product may be of a soft or a crisp character, either of a white, light or dark type. Examples are steamed or baked bread (in particular white, whole-meal or rye bread), typically in the form of loaves or rolls.

Modified AZCL-arabinoxylan from Wheat Assay pH 6.0

Substrate:

0.2% AZCL-Arabinoxylan from wheat (Megazyme) in 0.2 M Na-phosphate buffer pH 6.0+0.01% Triton-x-100.

Standard:

BioFeed Wheat (product of Novozymes A/S), diluted in 0.01% Triton X-100. FXU/ml: 0.05; 0.10; 0.15; 0.20; 0.25; 0.30; 0.40.

Method:

1. 900 µl substrate is preheated to 37° C. in a thermomixer
2. 100 µl sample is added
3. Incubate for 15 min at 37° C. at maximum speed
4. on ice for 2 min
5. spin 1 min 20.000×G
6. 2×200 µl supernatant is transferred to a micro titter plate
7. Endpoint OD 590 nm is measured.

EXAMPLES

Example 1

Production of xylanase

Cloning of *Paenibacillus Pabuli* GH 11 Xylanase

Chromosomal DNA of *Paenibacillus pabuli* strain DSM 16232 was isolated by QIAmp Tissue Kit (Qiagen, Hilden, Germany). A linear integration vector-system was used for the expression cloning of the gene. The linear integration construct was a PCR fusion product made by fusion of the gene between two *Bacillus subtils* homologous chromosomal regions along with a strong promoter and a chloramphenicol resistance marker. The fusion was made by SOE PCR (Horton, R. M., Hunt, H. D., Ho, S. N., Pullen, J. K. and Pease, L. R. (1989), Engineering hybrid genes without the use of restriction enzymes, gene splicing by overlap extension, Gene 77: 61-68). The SOE PCR method is also described in WO 2003095658. The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as marker. (Described in eg. Diderichsen, B.; Poulsen, G. B.; Joergensen, S. T.; A useful cloning vector for *Bacillus subtilis*. Plasmid 30:312 (1993)). The final gene construct was integrated on the *Bacillus* chromosome by homologous recombination into the pectate lyase locus.

First 3 fragments were PCR amplified: the gene fragment with specific primers oth62 (SEQ ID NO.: 3) and oth63 (SEQ ID NO.: 4) on genomic DNA from *Paenibacillus pabuli*. The upstream flanking fragment was amplified with the primers 260558 (SEQ ID NO.: 5) and UpN 1361 (SEQ ID NO.: 6) and the downstream flanking fragment was amplified with the primers 260559 (SEQ ID NO.: 7) and DwC 1361 (SEQ ID NO.: 8) from genomic DNA of the strain iMB1361 (described in WO 2003095658).

The DNA fragments were amplified with "Expand High Fidelity PCR System" (Boehringer Mannheim, Germany) using the following conditions: 94° C. for 2 min followed by 10 cycles of (94° C. for 15 sec, 55° C. for 30 sec, 68° C. for 4 min) followed by 20 cycles of (94° C. for 15 sec, 55° C. for 30 sec, 68° C. for 4 min (+20 sec pr cycle)) and ending with one cycle at 68° C. for 10 min. The 3 resulting fragments were mixed in equal molar ratios and a new PCR reaction was run under the following conditions: initial 2 min. at 94° C., followed by 10 cycles of (94° C. for 15 sec., 55° C. for 45 sec., 68° C. for 5 min.), 10 cycles of (94° C. for 15 sec., 55° C. for 45 sec., 68° C. for 8 min.), 15 cycles of (94° C. for 15 sec., 55° C. for 45 sec., 68° C. for 8 min. in addition 20 sec. extra pr cycle). After the 1$^{st}$ cycle the two end primers 260558 (SEQ ID NO.: 5) and 260559 (SEQ ID NO.: 7) were added (20 pMol of each). Two micro-I of the PCR product was transformed into *Bacillus subtilis* and transformants were selected on LB-plates containing chloramphenicol (6 µg/ml medium). A clone containing the construct without mutations leading to amino acid changes was selected for fermentation in liquid media.

The supernatant was analyzed for xylanase activity with modified AZCL-arabinoxylan as substrate by the assay described above and had around 150 FXU/ml:

Fermentation

The clone was streaked on an LB-agar plate with 6 micro g/ml chloramphenicol from −80° C. stock, and grown overnight at 37° C. The colonies were transferred to 100 ml PS-1 media supplemented with 6 micro g/ml chloramphenicol in a 500 ml shaking flask.

Composition of PS-1 medium:

| | |
|---|---|
| Saccharose | 100 g/l |
| Soy Bean Meal | 40 g/l |

-continued

| | |
|---|---|
| $Na_2HPO_4$, 12 $H_2O$ | 10 g/l |
| Pluronic ™ | 0.1 ml/l |

The culture was shaken at 30° C. at 275 rpm for 3 days. The cells were spun down and the enzyme purified from the supernatant.

Example 2

Purification of xylanase

The fermentation broth from Example 1 was filtered through filter paper and finally a blank filtration. Ammonium sulphate was added to a final concentration of 3.0 M and incubated for 30 min at room temperature. After 30 min centrifugation at 10000 g, the precipitate was solubilized with 10 mM sodium acetate pH 5.0 and dialyzed against 10 mM sodium acetate pH 5.0. After dialysis the sample was applied on a S-Sepharose column (Amersham Pharmacia Biotech 2.6 cm×10 cm) equilibrated with 10 mM sodium acetate pH 5.0. Elution was performed with a linear gradient from 0-1 M NaCl in 10 mM sodium acetate pH 5.0. Fractions containing xylanase activity were pooled and stored at −20° C. This preparation was used in Example 3.

Example 3

Effect of xylanase on Freshness of Bread

Bread were baked according to the sponge & dough method.

| Recipes | |
|---|---|
| | % on flour basis |
| Sponge | |
| Soya oil | 2.5 |
| SSL | 0.38 |
| Yeast | 5 |
| Wheat flour | 60 |
| Water | 62 |
| Dough | |
| Ascorbic acid | optimized for each flour |
| ADA | 20 ppm |
| Salt | 2 |
| Syrup | 7 (dry substance) |
| Water | to be optimized for each flour |
| Wheat flour | 40 |
| Calcium propionate | 025 |

Sponge

Scaling of ingredients, addition of yeast, water, flour, SSL and oil into mixer bowl Mixing 90 rpm for 1 minutes, 150 rpm for 4 minutes. The sponge is weighted, the temperature is measured and the sponge is placed in a bowl and fermented for 3 hours at 27° C., 86% RH.

Dough

Addition of ingredients and the sponge into the mixer bowl. The sponge and ingredients are mixed together 90 rpm for 9 minutes The temperature is measured, dough characteristics are evaluated, the dough is scaled into smaller pieces of 435 g each.

The dough rests on the table for 10 minutes

Doughs are sheeted and molded.

Fermentation for 55 minutes at 42° C. and 86% RH.

Bread are baked at 200° C. for 22 minutes

Enzymes were dosed at 2 mg of xylanase of the invention per kg of flour together with 400 MANU/kg of Novamyl. A control was made with 200 FXU/kg of the prior-art xylanase Shearzyme (product of Novozymes A/S) together with 400 MANU/kg of Novamyl.

Bread was stored at room temperature until analysis.

Texture and water migration by NMR were measured on day 7, 14 and 21. A small sensory evaluation of softness and moistness was performed on day 21.

Results

Firmness of the loaves was measured as described in WO 9953769 The results were as follows:

| Novamyl dosage MANU/kg | Xylanase of invention mg/kg | Prior-art xylanase FXU/kg | Firmness after 7 days g | Firmness after 14 days g | Firmness after 21 days g |
|---|---|---|---|---|---|
| 400 | 2 | 0 | 460 | 663 | 922 |
| 400 | 0 | 200 | 475 | 754 | 1058 |

Elasticity of the loaves was measured as described in U.S. Pat. No. 6,162,628. The results were as follows:

| Novamyl dosage MANU/kg | Xylanase of invention mg/kg | Prior-art xylanase FXU/kg | Elasticity after 7 days % | Elasticity after 14 days % | Elasticity after 21 days % |
|---|---|---|---|---|---|
| 400 | 2 | 0 | 48.5 | 46.8 | 43.1 |
| 400 | 0 | 200 | 44.9 | 44.9 | 42.2 |

The data show that the effect of the xylanase of the invention together with Novamyl on firmness and elasticity outperforms the combination the prior-art xylanase and Novamyl.

The mobility of free water was determined as described by P. L. Chen, Z. Long, R. Ruan and T. P. Labuza, Nuclear Magnetic Resonance Studies of water Mobility in Bread during Storage. Lebensmittel Wissenschaft und Technologie 30, 178-183 (1997). The results were as follows:

| Novamyl dosage MANU/kg | Xylanase of invention mg/kg | Prior-art xylanase FXU/kg | Free water after 7 days microseconds | Free water after 14 days microseconds | Free water after 21 days microseconds |
|---|---|---|---|---|---|
| 400 | 2 | 0 | 7632 | 6800 | 6450 |
| 400 | 0 | 200 | 7725 | 6438 | 6034 |

The data show that the xylanase of the invention increases the amount of free water more than the prior-art xylanase. The amount of free water has been described in literature to correlate to moistness of bread crumb.

The ranking from the small sensory evaluation of softness and moistness on day 21 showed that bread crumb made with the xylanase of the invention together with Novamyl was perceived as more moist than bread made with the prior-art xylanase and Novamyl.

The invention claimed is:

1. A process for preparing a dough-based product, comprising adding a polypeptide having xylanase activity, which has at least 98% identity to the sequence of amino acids 1-182 of SEQ ID NO: 2, to a dough in an amount effective for increasing the shelf-life of the dough-based product prepared from the dough, leavening, and baking the dough.

2. The process of claim 1, wherein the polypeptide comprises the sequence of amino acids 1-182 of SEQ ID NO: 2.

3. The process of claim 1, which further comprises adding an exo-acting maltogenic alpha-amylase to the dough.

4. An isolated polypeptide having xylanase activity, which has at least 98% identity to the sequence of amino acids 1-182 of SEQ ID NO: 2.

5. The polypeptide of claim 4, which comprises the sequence of amino acids 1-182 of SEQ ID NO: 2.

6. A composition which comprises flour and a polypeptide of claim 4.

7. The composition of claim 6 which is a dough.

8. A granulate or agglomerated powder comprising a polypeptide of claim 4.

* * * * *

SEQUENCE LISTING

<160> NUMBER OF SEQ ID NOS: 8

<210> SEQ ID NO 1
<211> LENGTH: 630
<212> TYPE: DNA
<213> ORGANISM: Paenibacillus pabuli
<220> FEATURE:
<221> NAME/KEY: sig_peptide
<222> LOCATION: (1)..(84)
<220> FEATURE:
<221> NAME/KEY: CDS
<222> LOCATION: (1)..(630)
<220> FEATURE:
<221> NAME/KEY: mat_peptide
<222> LOCATION: (85)..(630)

<400> SEQUENCE: 1

```
atg ttt aaa ttc gga aaa aaa ttg tta act gtt gtc ctt gcc gct tcc     48
Met Phe Lys Phe Gly Lys Lys Leu Leu Thr Val Val Leu Ala Ala Ser
        -25                 -20                 -15 atg agt ttt ggt gta ttc gcc gct acg aca ggt gct aca gat tac tgg     96
Met Ser Phe Gly Val Phe Ala Ala Thr Thr Gly Ala Thr Asp Tyr Trp
    -10                  -5              -1  1 cag aac tgg aca gat ggc ggg gt act gtt aat gcc gtg aac ggt tcg    144
Gln Asn Trp Thr Asp Gly Gly Gly Thr Val Asn Ala Val Asn Gly Ser
  5               10                  15                  20 gga gga aac tac agt gta aac tgg cag aac acg ggg aac ttt gtt gtc    192
Gly Gly Asn Tyr Ser Val Asn Trp Gln Asn Thr Gly Asn Phe Val Val
              25                  30                  35 ggt aaa ggg tgg act tac ggt aca cct aat cgt gta gtg aat tac aat    240
Gly Lys Gly Trp Thr Tyr Gly Thr Pro Asn Arg Val Val Asn Tyr Asn
          40                  45                  50 gcg ggt gta ttc tct cca tcc ggc aac gga tat ttg acg ttt tac ggg    288
Ala Gly Val Phe Ser Pro Ser Gly Asn Gly Tyr Leu Thr Phe Tyr Gly
              55                  60                  65 tgg aca cgg aat gca ctt att gaa tac tac gtg gtg gat aac tgg gga    336
Trp Thr Arg Asn Ala Leu Ile Glu Tyr Tyr Val Val Asp Asn Trp Gly
          70                  75                  80 aca tac cgg cca acc gga aca tac aaa ggc aca gta acc agt gat ggt    384
Thr Tyr Arg Pro Thr Gly Thr Tyr Lys Gly Thr Val Thr Ser Asp Gly
85                  90                  95                 100 ggc aca tat gac atc tat act acg atg aga tac aat cag cca tcc att    432
Gly Thr Tyr Asp Ile Tyr Thr Thr Met Arg Tyr Asn Gln Pro Ser Ile
                105                 110                 115 gac ggg tat tca aca ttc ccg caa tac tgg agt gtt aga caa tcc aaa    480
Asp Gly Tyr Ser Thr Phe Pro Gln Tyr Trp Ser Val Arg Gln Ser Lys
            120                 125                 130 cgt cca atc ggt gta aat tcc caa att acg ttc cag aat cac gta aat    528
Arg Pro Ile Gly Val Asn Ser Gln Ile Thr Phe Gln Asn His Val Asn
        135                 140                 145 gcg tgg gcg agc aag ggc atg tac ttg ggt aac agc tgg tcc tat caa    576
Ala Trp Ala Ser Lys Gly Met Tyr Leu Gly Asn Ser Trp Ser Tyr Gln
    150                 155                 160 gtg atg gcc acc gaa gga tat caa agt agc ggt agt tcg aat gtg act    624
Val Met Ala Thr Glu Gly Tyr Gln Ser Ser Gly Ser Ser Asn Val Thr
165                 170                 175                 180 gtt tgg                                                             630
Val Trp
```

<210> SEQ ID NO 2
<211> LENGTH: 210
<212> TYPE: PRT

<213> ORGANISM: Paenibacillus pabuli

<400> SEQUENCE: 2

```
Met Phe Lys Phe Gly Lys Lys Leu Leu Thr Val Val Leu Ala Ala Ser
        -25                 -20                 -15
Met Ser Phe Gly Val Phe Ala Ala Thr Thr Gly Ala Thr Asp Tyr Trp
        -10                 -5                  -1  1
Gln Asn Trp Thr Asp Gly Gly Thr Val Asn Ala Val Asn Gly Ser
  5                  10                  15                  20
Gly Gly Asn Tyr Ser Val Asn Trp Gln Asn Thr Gly Asn Phe Val Val
                25                  30                  35
Gly Lys Gly Trp Thr Tyr Gly Thr Pro Asn Arg Val Val Asn Tyr Asn
                40                  45                  50
Ala Gly Val Phe Ser Pro Ser Gly Asn Gly Tyr Leu Thr Phe Tyr Gly
                55                  60                  65
Trp Thr Arg Asn Ala Leu Ile Glu Tyr Val Val Asp Asn Trp Gly
 70                  75                  80
Thr Tyr Arg Pro Thr Gly Thr Tyr Lys Gly Thr Val Thr Ser Asp Gly
 85                  90                  95                  100
Gly Thr Tyr Asp Ile Tyr Thr Thr Met Arg Tyr Asn Gln Pro Ser Ile
                105                 110                 115
Asp Gly Tyr Ser Thr Phe Pro Gln Tyr Trp Ser Val Arg Gln Ser Lys
                120                 125                 130
Arg Pro Ile Gly Val Asn Ser Gln Ile Thr Phe Gln Asn His Val Asn
                135                 140                 145
Ala Trp Ala Ser Lys Gly Met Tyr Leu Gly Asn Ser Trp Ser Tyr Gln
                150                 155                 160
Val Met Ala Thr Glu Gly Tyr Gln Ser Ser Gly Ser Ser Asn Val Thr
165                 170                 175                 180
Val Trp
```

<210> SEQ ID NO 3
<211> LENGTH: 48
<212> TYPE: DNA
<213> ORGANISM: Artificial
<220> FEATURE:
<223> OTHER INFORMATION: Primer oth62

<400> SEQUENCE: 3
gttcatcgat cgcatcggct acagattact ggcagaactg gacagatg                    48

<210> SEQ ID NO 4
<211> LENGTH: 49
<212> TYPE: DNA
<213> ORGANISM: Artificial
<220> FEATURE:
<223> OTHER INFORMATION: Primer oth63

<400> SEQUENCE: 4
ggagcggatt gaacatgcga ttaccaaaca gtcacattcg aactaccgc                   49

<210> SEQ ID NO 5
<211> LENGTH: 21
<212> TYPE: DNA
<213> ORGANISM: Artificial
<220> FEATURE:
<223> OTHER INFORMATION: Primer 260558

<400> SEQUENCE: 5
gagtatcgcc agtaaggggc g                                                 21

```
<210> SEQ ID NO 6
<211> LENGTH: 20
<212> TYPE: DNA
<213> ORGANISM: Artificial
<220> FEATURE:
<223> OTHER INFORMATION: Primer UpN 1361

<400> SEQUENCE: 6
agccgatgcg atcgatgaac                                              20

<210> SEQ ID NO 7
<211> LENGTH: 23
<212> TYPE: DNA
<213> ORGANISM: Artificial
<220> FEATURE:
<223> OTHER INFORMATION: Primer 260559

<400> SEQUENCE: 7
gcagccctaa aatcgcataa agc                                          23

<210> SEQ ID NO 8
<211> LENGTH: 23
<212> TYPE: DNA
<213> ORGANISM: Artificial
<220> FEATURE:
<223> OTHER INFORMATION: Primer DwC 1361

<400> SEQUENCE: 8
taatcgcatg ttcaatccgc tcc                                          23
```